(12) United States Patent
Shigehisa

(10) Patent No.: US 11,490,788 B2
(45) Date of Patent: Nov. 8, 2022

(54) ENDOSCOPE APPARATUS

(71) Applicant: Evident Corporation, Nagano (JP)

(72) Inventor: Yoshiyuki Shigehisa, Fuchu (JP)

(73) Assignee: EVIDENT CORPORATION, Nagano (JP)

( * ) Notice: Subject to any disclaimer, the term of this patent is extended or adjusted under 35 U.S.C. 154(b) by 575 days.

(21) Appl. No.: 16/515,100

(22) Filed: Jul. 18, 2019

(65) Prior Publication Data
US 2019/0357753 A1 Nov. 28, 2019

Related U.S. Application Data

(63) Continuation of application No. PCT/JP2017/042175, filed on Nov. 24, 2017.

(30) Foreign Application Priority Data

Jan. 18, 2017 (JP) .............................. JP2017-006459

(51) Int. Cl.
*A61B 1/00* (2006.01)
(52) U.S. Cl.
CPC ...... *A61B 1/00059* (2013.01); *A61B 1/00096* (2013.01); *A61B 1/00101* (2013.01)
(58) Field of Classification Search
CPC ............ A61B 1/00059; A61B 1/00096; A61B 1/00101; A61B 1/00009; A61B 1/00186;
(Continued)

(56) References Cited

U.S. PATENT DOCUMENTS

2004/0070668 A1 4/2004 Abe
2005/0014996 A1 1/2005 Konomura et al.
(Continued)

FOREIGN PATENT DOCUMENTS

EP 3017747 A1 5/2016
JP H04-51212 A 2/1992
(Continued)

OTHER PUBLICATIONS

International Search Report dated Feb. 13, 2018 issued in PCT/JP2017/042175.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope apparatus includes an identification unit provided in each of a plurality of optical adaptors, an MMA connected in parallel to the identification unit, an MMA drive circuit that is provided in a main body portion and applies a drive signal for driving the MMA through a pair of conductive wires, a sine-wave generation circuit that is provided in the main body portion and applies an alternating signal to the identification unit through a pair of conductive wires in a state where any one of the plurality of optical adaptors is mounted at a distal end portion, and CPU that is provided in the main body portion and measures an input impedance of the pair of conductive wires at a frequency of the alternating current signal to perform individual identification of the optical adaptor mounted at the distal end portion based on a measurement result.

15 Claims, 10 Drawing Sheets

(58) Field of Classification Search
CPC ............ A61B 1/00006; A61B 1/00193; G02B 23/2476
USPC ........................................................ 600/118
See application file for complete search history.

(56) References Cited

U.S. PATENT DOCUMENTS

2009/0284588 A1    11/2009  Matsui
2016/0087584 A1 *  3/2016  Matsumoto ............ H03B 5/368 331/48
2016/0119521 A1    4/2016  Zen

FOREIGN PATENT DOCUMENTS

| | | | |
|---|---|---|---|
| JP | H04-329510 | A | 11/1992 |
| JP | 2002-174881 | A | 6/2002 |
| JP | 2002174881 | A * | 6/2002 |
| JP | 2004-049249 | A | 2/2004 |
| JP | 2004-313241 | A | 11/2004 |
| JP | 2006-047335 | A | 2/2006 |
| JP | 2007-044073 | A | 2/2007 |
| JP | 2008-188239 | A | 8/2008 |
| JP | 4783084 | B2 * | 9/2011 |
| JP | 4783084 | B2 | 9/2011 |
| JP | 2013-254034 | A | 12/2013 |
| JP | 2013254034 | A * | 12/2013 |
| WO | WO 2015/001852 | A1 | 1/2015 |

* cited by examiner

WHEN CABLE IS LONG AND IDENTIFICATION RESISTANCE IS LARGE

WHEN CABLE IS LONG AND IDENTIFICATION RESISTANCE IS SMALL

WHEN CABLE IS SHORT AND IDENTIFICATION RESISTANCE IS LARGE

WHEN CABLE IS SHORT AND IDENTIFICATION RESISTANCE IS SMALL

FIG. 5A

| INPUT IMPEDANCE(Z(s)) | IDENTIFICATION RESISTANCE R1(ZI) |
|---|---|
| $Z(s)1 \sim Z(s)1'$ | $zI1$ |
| $Z(s)2 \sim Z(s)2'$ | $zI2$ |
| $Z(s)3 \sim Z(s)3'$ | $zI3$ |
| ⋮ | ⋮ |
| $Z(s)n \sim Z(s)n'$ | $zIn$ |

WHEN IDENTIFICATION RESISTANCE IS LARGE

WHEN IDENTIFICATION RESISTANCE IS SMALL

ENDOSCOPE APPARATUS

CROSS REFERENCE TO RELATED APPLICATION

This application is a continuation application of PCT/JP2017/042175 filed on Nov. 24, 2017 and claims benefit of Japanese Application No. 2017-006459 filed in Japan on Jan. 18, 2017, the entire contents of which are incorporated herein by this reference.

BACKGROUND OF THE INVENTION

1. Field of the Invention

The present invention relates to an endoscope apparatus in which an optical adaptor is freely detachably attachable to a distal end portion of an insertion portion.

2. Description of the Related Art

Conventionally, endoscope apparatus having endoscopes have been widely used which are capable of observing body cavity visceral organs, etc., by inserting an elongated insertion portion into a body cavity, and performing various therapeutic treatments by using a treatment tool inserted into a treatment tool channel as needed. In the industrial field, endoscope apparatuses having industrial endoscopes have also been widely used for observation and inspection of flaws, corrosion and the like inside boilers, turbines, engines, chemical plants and the like.

The distal end portion of an industrial endoscope is generally designed so that an optical adaptor configured to change optical characteristics is detachably attachable to the distal end portion. The endoscope can acquire an optimal image according to an inspection application condition, such as a front-view image, a side-view image, an image in which the focal point is near the near point, or an image in which the focal point is near the far point, depending on the type of an optical adaptor to be attached. Furthermore, an optical adaptor is known which is provided with right and left optical systems to have a function of obtaining right and left images with parallax and measuring the dimension of an image by applying the principle of triangulation.

A plurality of types of optical adaptors are selected by an inspector, and attached to equipment by screwing, but it is difficult to determine from exterior identification marks which types of optical adaptors these selected optical adaptors are, and an optical adaptor having a specification different from an inspection intention may be erroneously attached. Therefore, in recent endoscopes, a resistance element configured to determine the type of an optical adaptor is mounted inside the optical adaptor, thereby providing the endoscopes with a function of detecting the resistance value of the resistance element when the apparatus main body is activated or the optical adaptor is attached, and automatically determining the type of the optical adaptor (for example, see Japanese Patent No. 4783084).

In the endoscope apparatus of this Japanese Patent No. 4783084, the distal end portion and the optical adaptor are connected to each other by two connecting wires and a terminal structure, and the optical adaptor is provided with a resistor configured to determine the type of the optical adaptor in parallel with an illumination LED. This endoscope apparatus is capable of realizing two modes with the two connecting wires and the terminal structure by switching the two modes of a light emission mode of LED and a type identification mode of the optical adaptor.

An endoscope apparatus in which an actuator mechanism is provided in an optical adaptor to switch optical characteristics inside the optical adaptor has been recently well known. In this endoscope apparatus, by controlling the movement of a shutter configured to switch a lens or an optical path inside the optical adaptor, for example, it is possible to switch a plurality of types of observation images such as near-point to far-point, front-view to side-view, etc., without replacing the optical adaptor (for example, see International Publication No. 2015/001852).

The endoscope apparatus of this International Publication No. 2015/001852 discloses a mechanism configured to move a shutter between a first position and a second position, the shutter being configured to switch an optical path by using an electromagnetic actuator. The electromagnetic actuator is a drive mechanism using a coil and a magnet, and controls the position of the shutter to which the magnet is fixed, by a magnetic field generated according to the direction and magnitude of a current applied to the coil.

As another technique that determines the type of optical adaptor is disclosed as a technique in which an oscillation circuit and a power source configured to drive the oscillation circuit are connected in parallel with an illumination LED inside the optical adaptor (for example, see Japanese Patent Application Laid-Open Publication No. 2013-254034).

The endoscope apparatus disclosed in Japanese Patent Application Laid-Open Publication No. 2013-254034 has a mechanism configured to detect an alternating current signal output of the oscillation circuit on a main body side and determine the type of the optical adaptor under a power supply condition in which LED does not perform a light emitting operation. The voltage of the power supply to be supplied to the circuit is switched between high and low levels by utilizing the property that the power supply voltage when LED is turned on is higher than the power supply voltage of the oscillation circuit, thereby switching an LED light emission operation mode and a type determination operation mode of the optical adaptor. This makes it possible to perform light emission of LED and determination of the type of the optical adaptor with the two connecting wires and the terminal structure.

For example, the endoscope apparatus of Japanese Patent No. 4783084 performs lighting of LED and determination of the type of an optical adaptor with two terminals. In other words, in consideration of reduction of the diameter of the insertion portion of the endoscope, it is required to set the number of contact terminals of the optical adaptor to two. When an optical adaptor having both functions of determining the type of the optical adaptor and switching the optical characteristics by using an actuator is realized by two terminals, the two terminals are required to be provided in consideration of reduction of the diameter of the insertion portion.

As disclosed in Japanese Patent No. 4783084, when a resistor for type determination is provided in the optical adaptor and a DC voltage between both the ends of the resistor is detected to perform the determination processing of the optical adaptor, The resistor to be used is configured so that a plurality of types of resistors in a range of several k Ω to several M Ω are selectively used depending on the type of the optical adaptor.

SUMMARY OF THE INVENTION

An endoscope apparatus according to an aspect of the present invention that includes an insertion portion including a distal end portion to which any one of a plurality of optical adaptors is freely detachably attachable, and a proximal end portion connected to an apparatus main body portion, includes: an identification impedance element that is provided in at least one of the plurality of optical adaptors and configured to perform individual identification of each optical adapter; an electric element that is provided in each of the plurality of optical adaptors and connected in parallel to the identification impedance element; a drive circuit that is provided in the apparatus main body portion and configured to apply a drive signal for driving the electric element through a pair of conductive wires inserted through the insertion portion; an oscillation circuit that is provided in the apparatus main body portion and configured to apply an alternating signal to the identification impedance element through the pair of conductive wires in a state where any one of the plurality of optical adaptors is mounted at a distal end portion of the insertion portion; a measurement circuit that is provided in the apparatus main body portion and configured to measure an input impedance of the pair of conductive wires at a frequency of the alternating current signal; and an identification circuit that is provided in the apparatus main body portion and configured to perform individual identification of an optical adaptor mounted at the distal end portion of the insertion portion based on a measurement result of the measurement circuit.

BRIEF DESCRIPTION OF THE DRAWINGS

FIG. 5A is a diagram showing an example of an identification table in which the relationship between the input impedance and a resistance value of an identification resistor is tabulated;

DETAILED DESCRIPTION OF THE PREFERRED EMBODIMENTS

Embodiments according to the present invention will be described hereunder with reference to the drawings.

First Embodiment

Figure 1:
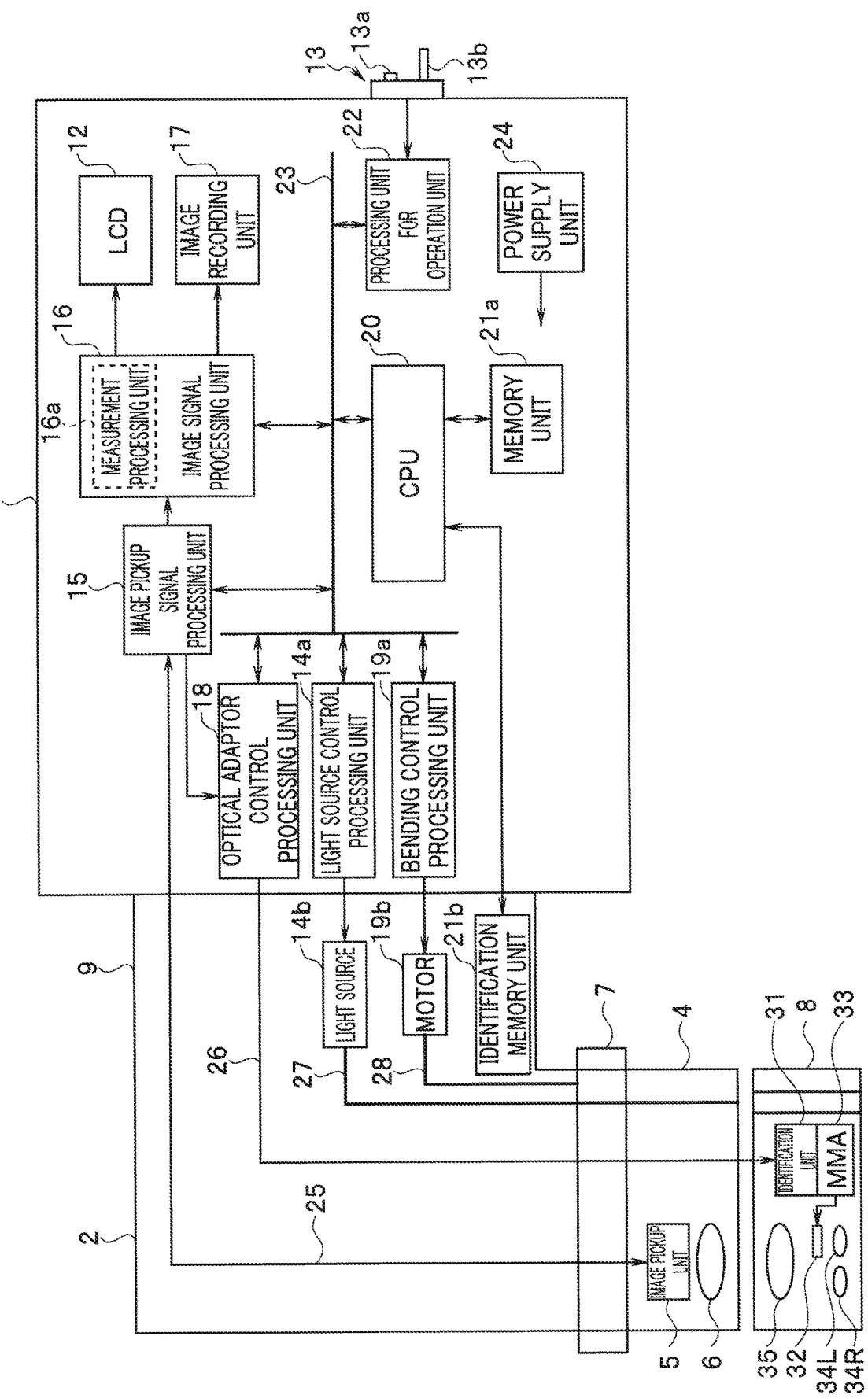
FIG. 1 is a diagram showing a configuration of an endoscope apparatus according to a first embodiment.

FIG. 1 is a diagram showing a configuration of an endoscope apparatus according to a first embodiment.

As shown in FIG. 1, an endoscope apparatus 1 is configured to include an elongated insertion portion 2 having flexibility and an apparatus main body (hereinafter merely referred to as a main body portion) 3 to which a proximal end portion of the insertion portion 2 is connected.

The insertion portion 2 is configured to be attachable to and detachable from the main body portion 3, and the insertion portion 2 and the main body portion 3 are configured so that various insertion portions having different lengths, diameters, observation functions, etc., can be appropriately attached to the main body portion 3 to be replaceable.

The distal end portion 4 of the insertion portion 2 is provided with an image pickup unit 5 having an image pickup device such as CCD or CMOS, and an objective lens 6 arranged on an image pickup surface side of the image pickup unit 5. Furthermore, a bending portion 7 configured to cause the distal end portion 4 to be bent in a desired direction is provided on a proximal end side of the distal end portion 4 of the insertion portion 2.

A signal line 25, a transmission cable 26, a light guide 27 and a bending wire 28 are inserted into the insertion portion 2.

The signal line 25 is connected to the image pickup unit 5. The transmission cable 26 is connected to an identification unit 31 and an MMA 33 of the optical adaptor 8 described later. The light guide 27 is connected to a light source 14b described later. The distal end side of the bending wire 28 is connected to the bending portion 7, and the proximal end side is connected to a bending motor 19b described later.

The light source 14b, the bending motor 19b, and an identification memory unit 21b are provided at the proximal end portion 9 of the insertion portion 2.

The light source 14b emits illumination light configured to illuminate an object as an observation target, and is a xenon lamp, LED, a laser diode or the like, for example. The light source 14b is arranged to face a proximal end surface of the light guide 27.

The illumination light emitted from the light source 14b is emitted from the distal end portion 4 of the insertion portion 2 through the light guide 27 provided from the proximal end portion 9 to the distal end portion 4 in the insertion portion 2, and the object is irradiated with the illumination light. Note that the light source 14b is provided in the main body portion 3, but the light source 14b may be provided at the distal end portion 4 of the insertion portion 2, for example.

The bending motor 19b is a motor configured to bend the bending portion 7. The bending wire 28 inserted into the insertion portion 2 is connected to the bending motor 19b. When the bending motor 19b is driven to pull the bending wire 28, the bending portion 7 is bent, so that it is possible to bend the distal end portion 4 of the insertion portion 2 in a desired direction. Note that the bending motor 19 is merely described as a motor in FIG. 1.

Cable characteristic information as information unique to the insertion portion 2 and information such as the type and the number of pixels of the image pickup device in the image pickup unit 5 are stored in the identification memory unit 21b.

The distal end portion 4 of the insertion portion 2 is configured so that any one of the plurality of optical adaptors 8 is freely detachably attachable to the distal end portion 4.

A plurality of types of optical adaptors 8 exist, and it is possible to change various optical characteristics such as change of a view angle such as close-up, wide-angle, and enlargement (telephoto), and change of an observation direction such as front view, side view, and oblique view according to the type to be mounted at the distal end portion 4 of the endoscope 2. The inspector can select optical adaptors 8 having different optical characteristics and attach the selected optical adaptors 8 to the distal end portion 4 according to a location and a situation of an inspection.

The optical adaptor 8 includes an identification unit 31 configured to identify the type of the optical adaptor 8, etc., a shutter 32 configured to switch the optical path, a magnetic microactuator (hereinafter referred to as an MMA) 33 configured to drive the shutter 32, a left-eye lens 34L and a right-eye lens 34R which are two right-and-left observation optical systems, and an objective lens 35.

The main body portion 3 includes a liquid crystal panel (hereinafter, abbreviated as an LCD) 12 as a display unit on which an endoscopic image, an operation menu, and the like are displayed. A touch panel may be provided on the LCD 12. The main body portion 3 has an operation unit 13 configured to perform various operations. The operation unit 13 is configured to include an operation switch 13a configured to perform various operations of the endoscope apparatus 1 and a bending joystick 13b configured to bend the bending portion 7.

The main body portion 3 is configured to include a light source control processing unit 14a, an image pickup signal processing unit 15, an image signal processing unit 16, an image recording unit 17, an optical adaptor control processing unit 18, a bending control processing unit 19a, and a central processing unit (hereinafter referred to as a CPU) 20, a memory unit 21, a processing unit 22 for the operation unit, a bus 23, and a power supply unit 24.

Note that the light source control processing unit 14a, the image pickup signal processing unit 15, the image signal processing unit 16, the optical adaptor control processing unit 18, the bending control processing unit 19a, the CPU 20, and the processing unit 22 for the operation unit are mutually connected to one another via the bus 23.

The signal line 25 is connected to the image pickup signal processing unit 15, and the image pickup signal processing unit 15 is connected to the image pickup unit 5 of the distal end portion 4 through the signal line 25. The transmission cable 26 is connected to the optical adaptor control processing unit 18, and is connected to the identification unit 31 of the optical adaptor 8 and the MMA 33 via the transmission cable 26.

The light source control processing unit 14a outputs a drive signal for driving the light source 14b to the light source 14b. The light source 14b is driven by control of the light source control processing unit 14a and causes illumination light to be incident on a proximal end face of the light guide 27

Under control of the MMA 33, the shutter 32 provided in the optical adaptor 8 is selectively placed at a first position where an optical path passing through the left-eye lens 34L is blocked and a second position where an optical path passing through the right-eye lens 34R is blocked. As a result, return light from an object irradiated with the illumination light is incident to the image pickup unit 5 through the left-eye lens 34L, the objective lens 35 and the objective lens 6 or through the right-eye lens 34R, the objective lens 35 and the objective lens 6. The image pickup unit 5 converts an incident optical image of the object into an image pickup signal, and supplies the image pickup signal to the image pickup signal processing unit 15 via the signal line 25. The image pickup signal processing unit 15 outputs a drive signal to the image pickup unit 5, performs predetermined signal processing on the image pickup signal captured by the image pickup unit 5, and outputs the processed image pickup signal to the image signal processing unit 16.

The image signal processing unit 16 subjects the image pickup signal from the image pickup signal processing unit 15 to predetermined image signal processing to generate a signal to be displayed on the LCD 12 and/or a signal to be recorded on the image recording unit 17, and outputs the generated signal to the LCD 12 and/or the image recording unit 17. The image processing unit 16 also includes a measurement processing unit 16a that can perform various kinds of measurements from right and left object images captured by the image pickup unit 5 by using the principle of triangulation.

The LCD 12 displays a pickup image from the image signal processing unit 16. The image recording unit 17 records the pickup image from the image signal processing unit 16. Note that the image recording unit 17 may be a memory provided in the main body portion 3 or may be a memory card or the like which is detachable from the main body portion 3.

The optical adaptor control processing unit 18 generates determination information by detecting a signal necessary to identify the type of the optical adaptor 8 attached to the distal end portion 4 by the CPU 20 or by processing the detected signal. The optical adaptor control processing unit 18 also drives the MMA 33 to control the position of the shutter 32. Note that the details of the determination of the type of the optical adaptor 8 and the driving of the MMA 33 will be described later. The optical adaptor control processing unit 18 outputs the detected signal and the determination information to the CPU 20. The CPU 20 determines the type of the optical adaptor 8 based on the input signal and the determination information, and performs image processing and the like according to a determination result. The CPU 20 may display the identified type of the optical adaptor 8 on the LCD 12 via the image processing unit 16.

The bending control processing unit 19a drives the bending motor 19b according to a bending control signal from the processing unit 22 for the operation unit. The bending control processing unit 19a drives the bending motor 19b to pull the bending wire 28, whereby the distal end portion 4 of the insertion portion 2 can be bent in a desired direction.

The CPU 20 controls the entire main body portion 3. The memory unit 21 stores a program to be executed when the CPU 20 controls the entire main body portion 3. The memory unit 21 also temporarily stores data when the CPU 20 executes the program, calculation results, and the like.

The processing unit 22 for the operation unit outputs the bending control signal to the bending control processing unit 19a according to operation signals from the operation switch 13a of the operation unit 13 and the bending joystick 13b. The power supply unit 24 supplies power to various circuits of the main body portion 3.

Figure 2:
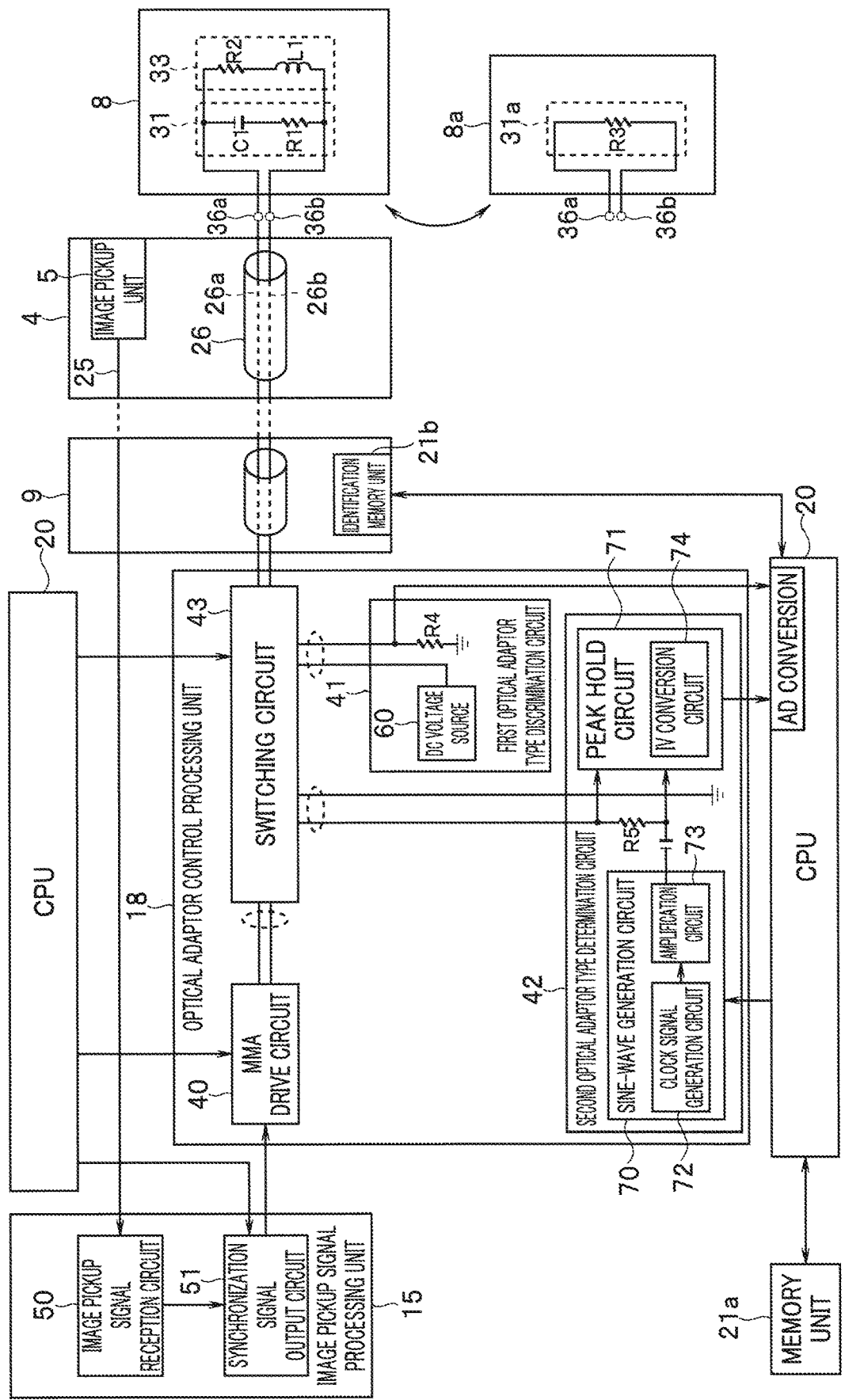
FIG. 2 is a diagram showing a detailed configuration of a main part of the endoscope apparatus 1 according to the first embodiment.

Next, the detailed configuration of a main part of the endoscope apparatus 1 will be described. FIG. 2 is a diagram showing a detailed configuration of the main part of the endoscope apparatus 1 according to the first embodiment.

A plurality of types of optical adaptors in which the MMA is mounted, the MMA is not mounted or the like exist as the optical adaptor to be mounted at the distal end portion 4 of the insertion portion 2. For example, as shown in FIG. 2, an optical adaptor 8 in which the identification unit 31 and the MMA 33 are mounted, and an optical adaptor 8a in which the MMA 33 is not mounted, and only the identification unit 31a is mounted exist as optical adaptors. These optical adaptors 8 and 8a are configured to be exchangeable and attachable to the distal end portion 4 of the insertion portion 2.

The optical adaptor 8 of the type in which the MMA is mounted has a configuration in which the identification unit 31 and the MMA 33 are connected in parallel. The identification unit 31 has a configuration in which a capacitor C1 and an identification resistor R1 are connected in series as an element for identification. The capacitor C1 and/or the identification resistor R1 constitute an identification impedance element for individual identification for the optical adaptor 8. The MMA 33 as an electric element is a component formed of a winding coil, and has a configuration in which an inductance L1 and a resistor R2 are connected in series, which is an equivalent circuit. On the other hand, the optical adaptor 8a of the type in which the MMA is not mounted has a configuration having one identification resistor R3 as an element for identification of the identification unit 31a.

The optical adaptor 8 has a two-terminal configuration having two connection terminals 36a and 36b, and is connected to the optical adaptor control processing unit 18 via the transmission cable 26 inserted into the insertion portion 2. The optical adaptor 8a also has a similar configuration, and has a two-terminal configuration having two connection terminals 36a and 36b. The transmission cable 26 includes signal lines 26a and 26b which are a pair of conductive wires to connect to the two connection terminals 36a and 36b, respectively. The optical adaptor 8 is connected to each circuit in the optical adaptor control processing unit 18 via the signal lines 26a and 26b of the transmission cable 26.

The optical adaptor control processing unit 18 includes an MMA drive circuit 40 configured to drive the MMA 33, a first optical adaptor type determination circuit 41 configured to determine the type of the optical adaptor 8 by using a direct current signal, a second optical adaptor type determination circuit 42 configured to determine the type of the optical adaptor 8 by using an alternating current signal, and a switching circuit 43.

Under the control of the CPU 20, the switching circuit 43 performs switching so as to connect any one circuit of the MMA drive circuit 40, the first optical adaptor type determination circuit 41 and the second optical adaptor type determination circuit 42 to the transmission cable 26. In other words, the switching circuit 43 controls so that the outputs of the MMA drive circuit 40, the first optical adaptor type determination circuit 41, and the second optical adaptor type determination circuit 42 are not simultaneously applied to the transmission cable 26.

The image pickup signal processing unit 15 is configured to include an image pickup signal reception circuit 50 and a synchronization signal output circuit 51. The image pickup signal reception circuit 50 performs reception processing for receiving through the signal line 25 an image pickup signal outputted from the image pickup unit 5 at the distal end portion 4 of the insertion portion 2. The image pickup signal reception circuit 50 generates a synchronization signal for determining an image pickup timing from the received image pickup signal, and outputs the generated synchronization signal to a synchronization signal output circuit 51. The CPU 20 outputs, to the synchronization signal output circuit 51, an instruction signal indicating whether to output the synchronization signal, in what mode the MMA 33 is driven, whether to switch the position of the shutter 32, etc.

The synchronization signal generation circuit 51 outputs a synchronization signal for driving the shutter 32 to the MMA drive circuit 40 of the optical adaptor control processing unit 18 based on the synchronization signal from the image pickup signal reception circuit 50 and the instruction signal from the CPU 20. As a result, the CPU 20 controls so that the image pickup operation of the image pickup unit 5 is not affected by the operation of the MMA 33.

The first optical adaptor type determination circuit 41 includes a DC voltage source 60 and a resistor R4 and applies a DC voltage generated by the DC voltage source 60 to the optical adaptor 8 to determine the type of the optical adaptor 8.

The second optical adaptor type determination circuit 42 includes a sine-wave generation circuit 70 and a peak hold circuit 71. The sine-wave generation circuit 70 includes a clock signal generation circuit 72 and an amplification circuit 73. The peak hold circuit 71 includes an IV conversion circuit 74, a circuit (not shown) configured to hold the peak value of the voltage amplitude of the sine-wave signal at the cable end portion, and a circuit (not shown) configured to perform IV conversion on the current flowing into the cable and then hold the peak value. R5 represents a current detection resistor required for the IV conversion. The second optical adaptor type determination circuit 42 applies an alternating current signal generated by the sine-wave generation circuit 70 to the optical adaptor 8 to determine the type of the optical adaptor 8

The CPU 20 outputs a setting signal for setting the current for the MMA drive circuit 40 to the MMA drive circuit 40. The CPU 20 outputs to the switching circuit 43 a selection signal for selecting which output out of the outputs of the MMA drive circuit 40, the first optical adaptor type determination circuit 41, and the second optical adaptor type determination circuit 42 is connected to the transmission cable 26. The CPU 20 further performs frequency setting necessary for the determination of the type of the optical adaptor 8 on the second optical adaptor type determination circuit 42. The CPU 20 performs AD conversion on detection signals outputted from the first optical adaptor type determination circuit 41 and the second optical adaptor type determination circuit 42 to determine the type of the optical adaptor 8 and determine whether the optical adaptor 8 is attached or detached. Note that when determining the type of the optical adaptor 8, the CPU 20 may read an identification table stored in the memory unit 21a or the identification memory unit 21b, and use the read identification table to determine the type of the optical adaptor 8. The identification table stored in the memory unit 21a or the identification memory unit 21b will be described later.

Here, the operations of the MMA drive circuit 40, the first optical adaptor type determination circuit 41, and the second optical adaptor type determination circuit 42 will be described in detail.

First, the MMA drive circuit 40 will be described. In the present embodiment, the MMA 33 is used to switch the right and left optical paths, and switches the position of the shutter 32 between the first position where the optical path passing through the left-eye lens 34L is blocked and the second position where the optical path passing through the right-eye lens 34R is blocked.

When the MMA 33 is driven, the switching circuit 43 is controlled under the control of the CPU 20 so that the output of the MMA drive circuit 40 is connected to the transmission cable 26. The MMA drive circuit 40 as a drive circuit applies a drive signal for driving the MMA 33 to the MMA 33 via the transmission cable 26. The drive signal outputted from the MMA drive circuit 40 has a pulse-like current waveform in both a positive direction and a negative direction, and the position of the shutter 32 is switched only during a period when a current in the positive direction or a current in the negative direction is applied.

For example, when the current in the positive direction is applied to the MMA 33 from the MMA drive circuit 40, the shutter 32 is switched to the first position where the optical path passing through the left-eye lens 34L is blocked. On the other hand, when the current in the negative direction is applied to the MMA 33 from the MMA drive circuit 40, the shutter 32 is switched to the second position where the optical path passing through the right-eye lens 34R is blocked. However, the shutter 32 is configured so that the shutter 32 cannot move any further when the shutter 32 reaches a butting mechanism portion (not shown) inside the optical adaptor 8. In a state where the shutter 32 has reached the butting mechanism portion, the shutter 32 is configured to keep the position without moving even when the pulse-like drive signal is not applied from the MMA drive circuit 40.

If an image of a transient state of the shutter 32 is picked up by the image pickup unit 5 when the MMA 33 is driven to switch the position of the shutter 32, an observation image in a disordered state is displayed on LCD 12. Therefore, the image pickup signal reception circuit 50 receives the image pickup signal outputted from the image pickup unit 5, generates a synchronization signal so that the position of the shutter 32 is switched during a blanking period in which the image pickup unit 5 does not perform exposure control, and outputs the generated synchronization signal to the synchronization signal output circuit 51. Then, the synchronization signal output circuit 51 outputs the synchronization signal to the MMA drive circuit 40 under the control of the CPU 20 so as to control so that an image of a transient state where the position of the shutter 32 is switched is not picked up by the image pickup unit 5.

Next, the first optical adaptor type determination circuit 41 will be described. When the type of the optical adaptor 8 is determined by the first optical adaptor type determination circuit 41, under the control of the CPU 20, the switching circuit 43 is controlled so that the output of the first optical adaptor type determination circuit 41 is connected to the transmission cable 26.

First, determination of the type of the optical adaptor 8a in which the MMA is not incorporated will be described. The first optical adaptor type determination circuit 41 applies the DC voltage from the DC voltage source 60 to the optical adaptor 8a. Then, a voltage divided by the identification resistor R3 provided in the optical adaptor 8a and the resistor R4 provided in the first optical adaptor type determination circuit 41 is inputted to the CPU 20. The CPU 20 detects the resistance value of the identification resistor R3 of the optical adaptor 8a according to the inputted voltage, and determines the type of the optical adaptor 8a based on the magnitude of the detected resistance value.

The first optical adaptor type determination circuit 41 can determine whether the optical adaptor mounted at the distal end portion 4 is an optical adaptor 8 in which the MMA 33 is incorporated or an optical adaptor 8a in which no MMA is incorporated.

The resistance value of the identification resistor R3 for identification is set to a large value of several k Ω to several M Ω. On the other hand, the MMA 33 is configured by a winding coil, and the resistance value of the resistor R2 is set to a small value of several Ω.

The identification unit 31 of the optical adaptor 8 and the MMA 33 are connected in parallel, and the combined resistance value of the identification unit 31 and the MMA 33 is smaller than the resistance value of the identification resistor R3 of the optical adaptor 8a in which no MMA is incorporated. Therefore, by determining whether the detected resistance value of the identification resistor R1 or R3 is smaller than a predetermined threshold value (Rth), the CPU 20 can determine whether the optical adaptor connected to the distal end portion 4 is an optical adaptor 8 in which the MMA 33 is incorporated or an optical adaptor 8a in which no MMA is incorporated. The predetermined threshold value (Rth) is determined in consideration of the resistance value of the resistance R2 of the winding coil of the MMA 33.

Next, the second optical adaptor type determination circuit 42 will be described. When the optical adaptor 8a in which no MMA is incorporated is connected to the distal end portion 4, as described above, the CPU 20 determines the type of the optical adaptor 8a from the detected resistance value of the identification resistor R3. On the other hand, when the optical adaptor 8 in which the MMA 33 is incorporated is connected to the distal end portion 4, the resistance value of the combined resistance of the identification unit 31 and the MMA 33 connected in parallel is smaller, and thus it is difficult to determine the type of the optical adaptor 8.

Therefore, when detecting that the optical adaptor 8 in which the MMA 33 is incorporated is connected to the distal end portion 4, the CPU 20 controls to perform the determination of the type by the second optical adaptor type determination circuit 42. When the type of the optical adaptor 8 is determined by the second optical adaptor type determination circuit 42, under the control of the CPU 20, the switching circuit 43 is controlled so that the output of the second optical adaptor type determination circuit 42 is connected to the transmission cable 26.

The sine-wave generation circuit 70 as an oscillation circuit is a circuit configured to input a sine-wave signal of a single frequency to the optical adaptor 8 through the transmission cable 26. The sine-wave generation circuit 70 includes a clock signal generation circuit 72 configured to generate a pulse-like clock signal, and an amplification circuit 73 configured to perform a predetermined waveform shaping on the pulse-like clock signal of the clock signal generation circuit 72 and output a sine-wave signal. Note that the circuit configuration for generating the sine-wave signal is not limited to the clock signal generation circuit 72 and the amplification circuit 73, but may also be another circuit configuration.

A terminal portion of the transmission cable 26 connected to the sine-wave generation circuit 70 is connected to the peak hold circuit 71. Thus, the sine-wave signal outputted from the sine-wave generation circuit 70 is inputted to the peak hold circuit 71.

The peak hold circuit 71 holds the peak value of the voltage amplitude of the sine-wave signal at the cable end portion, and the peak hold circuit 71 also performs IV conversion on the current flowing into the cable and then holds the peak value of the current amplitude. The peak hold circuit 71 outputs to the CPU 20 the held peak values of the voltage amplitude and the current amplitude. The CPU 20 converts the inputted peak values of the voltage amplitude and the current amplitude into input impedance, and determines the type of the optical adaptor 8 based on the input impedance value.

As described above, in the present embodiment, the alternating current signal is applied to the optical adaptor 8 from the second optical adaptor type determination circuit 42 of the main body portion 3, and the voltage between both the ends of the transmission cable 26 and an inflow current, in other words, the input impedance is measured, the state of the identification element (the resistance value of the identification resistor R1) in the identification unit 31 of the optical adaptor 8 is determined, and the type of the optical adaptor 8 is determined.

Note that the configuration for measuring the input impedance is not limited only to the above configuration, but may be a configuration for performing the measurement by using an alternating current bridge circuit used to measure the impedance, for example. In the alternating current bridge circuit, four impedance elements are connected in a bridge shape, and even when one of the impedance elements has an unknown value, it is possible to measure an unknown impedance by adjusting the remaining impedances and setting the currents among the terminals of the bridge circuit to zero. Since this technique is a well-known technique, details of the principle thereof are omitted here. Assuming that the input impedance of the cable in the case of the present invention is unknown, the measurement is performed by using the above circuit.

A circuit is further provided which keeps the voltage between both the ends of the terminal portions of the transmission cable 26 constant at all times, and only the inflow current is measured in that state, or conversely, it goes without saying that the impedance can be calculated by a method of keeping the current constant and measuring the voltage between both the ends.

The identification unit 31 includes a capacitor C1 and an identification resistor R1 as elements for identification, and the capacitor C1 and the identification resistor R1 are connected in parallel to the MMA 33. The capacitor C1 is provided to prevent the pulsed drive current from the MMA drive circuit 40 from flowing into the identification resistor R1 side when the MMA 33 is driven. Furthermore, in order to determine the type of the optical adaptor 8, the impedance of the capacitor C1 is set to a constant that is sufficiently negligible when the alternating current signal is applied from the sine-wave generation circuit 70. For example, by setting the frequency of the alternating current signal to about 10 MHz and setting the capacitance of the capacitor C1 to a value of about 0.1 μF, the impedance becomes a value of about 0.1Ω, which is a sufficiently negligible small value. Since the inductance L1 of the MMA 33 has a value of about 100 μH, the impedance becomes a large value of about several k Ω or more at the same frequency.

By selecting the resistance value of the identification resistor R1 of the identification unit 31 in the range from several tens of Ω to several hundreds of Ω, most of the alternating current signal applied to the optical adaptor 8 flows to the identification resistor R1 side. In other words, only the impedance of the identification resistor R1 is seen from the terminal portions of the transmission cable 26. As described above, by applying the alternating current signal generated in the second optical adaptor type determination circuit 42 to the optical adaptor 8, only the impedance of the identification resistor R1 of the identification unit 31, that is, the resistance value of the identification resistor R1, can be detected. Therefore, the type of the optical adaptor 8 can be determined according to the detected resistance value.

Figure 3:
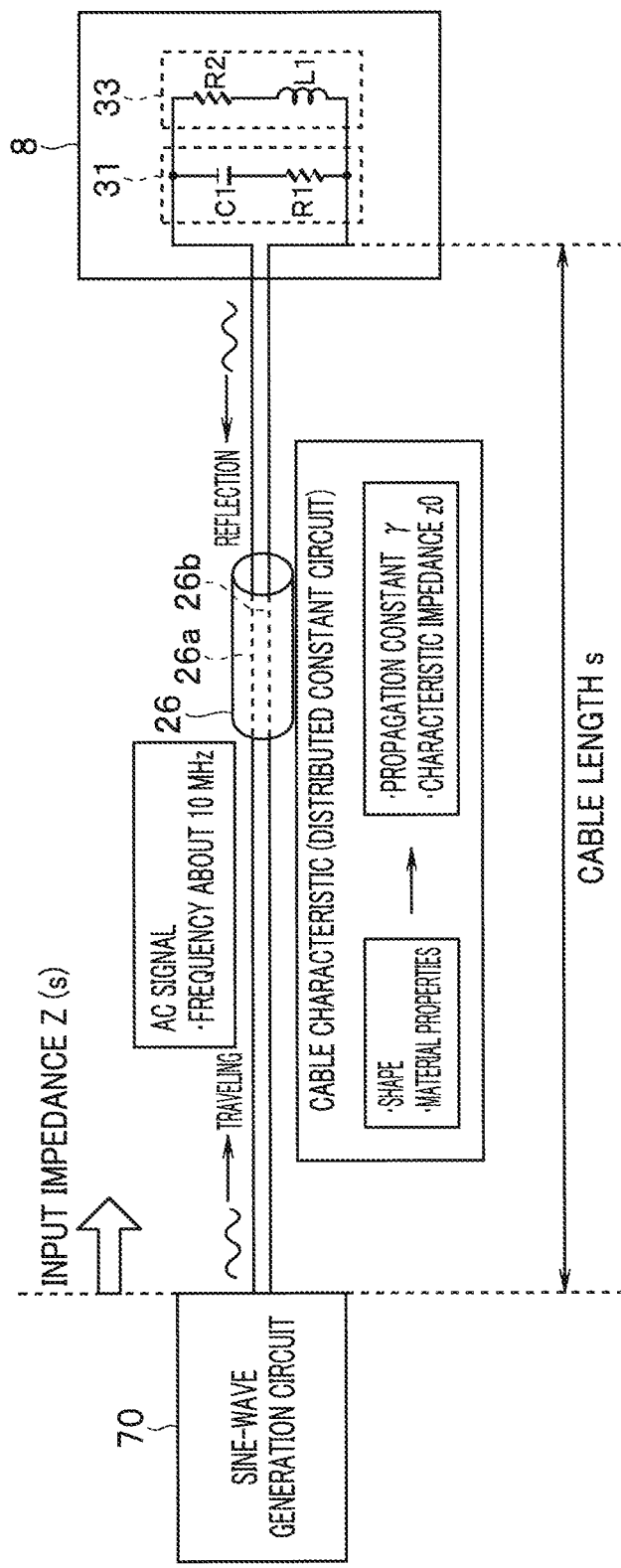
FIG. 3 is a schematic diagram showing an example of signal propagation between a sine-wave generation circuit 70 and an optical adaptor 8.

Next, signal propagation between the sine-wave generation circuit 70 and the optical adaptor 8 will be described with reference to FIG. 3. FIG. 3 is a schematic diagram showing an example of the signal propagation between the sine-wave generation circuit 70 and the optical adaptor 8.

As shown in FIG. 3, the sine-wave generation circuit 70 provided in the second optical adaptor type determination circuit 42 of the main body portion 3 generates an alternating current signal of about 10 MHz. The alternating current signal is propagated to the optical adaptor 8 attached to the distal end portion 4 through the transmission cable 26, and applied to the optical adaptor 8. At this time, a reflected wave is generated at the connection portion between the load of the optical adaptor 8 on the distal end side and the transmission cable 26 due to the difference in impedance.

When the load impedance of the optical adaptor 8 and the characteristic impedance of the transmission cable 26 are coincident with each other, the reflected wave is the smallest and becomes zero. When one of the load impedance of the optical adaptor 8 and the characteristic impedance of the transmission cable 26 is larger than the other, the reflected wave becomes large. Due to the influence of the reflected wave, an apparent impedance seen from the main body portion 3 side of the transmission cable 26 is increased or decreased by the load of the optical adaptor 8 at the distal end portion.

The frequency of the alternating current signal and the transmission path length (cable length s) exist as other factors for determining the influence of the reflected wave. The propagation speed of the alternating current signal is constant regardless of the frequency of the signal. In other words, the wavelength of the signal increases or decreases in inverse proportion to the frequency of the alternating current signal. As a result, the phase difference between the input signal and the reflected signal observed at the input end portion of the transmission cable 26 changes in accordance with the frequency of the signal and the length of the transmission cable 26.

Equation (1) is an equation which calculates the impedance seen from the input end portion of the transmission cable 26.

[Equation 1]

$$Z(s) = z0 \frac{z1 + z0\tanh ys}{z0 + z1\tanh ys} \quad (1)$$

In Equation (1), z0 represents the characteristic impedance of the transmission cable 26, and can be calculated from Equation (2).

[Equation 2]

$$z0 = \sqrt{\frac{R + j\omega L}{G + j\omega C}} \quad (2)$$

This Equation (2) shows the impedance when the transmission cable 26 is replaced with a distributed constant circuit which is captured as an aggregate of a minute resistor R, a capacitor C, an inductance L, and a conductance G.

In Equation (1), z1 represents the impedance on the load side (optical adaptor 8). In the present embodiment, the impedance on the load side is the resistance value of the identification resistor R1, but may be an impedance value including the values of the capacitor C1 and the inductance L1. γ in Equation (1) is a value which is called a propagation constant and can be calculated from Equation (3).

[Equation 3]

$$\gamma = \sqrt{(R+j\omega L)(G+j\omega C)} \quad (3)$$

This Equation (3) shows the attenuation characteristic of the signal when the transmission cable 26 is replaced with the distributed constant circuit as described above. Note that R, C, L, and G of Equation (2) and Equation (3) can be calculated from the shape and the material characteristics of the transmission cable 26.

FIG. 4A, FIG. 4B, FIG. 4C and FIG. 4D are diagrams showing examples of the input impedance characteristics. The input impedance characteristics in FIGS. 4A, 4B, 4C and 4D are obtained by calculating, from the equation (1) described above, the change of the input impedance with respect to the change of the frequency when the cable length s and the load impedance (the value of the identification resistance R1) are changed.

Figure 4A:
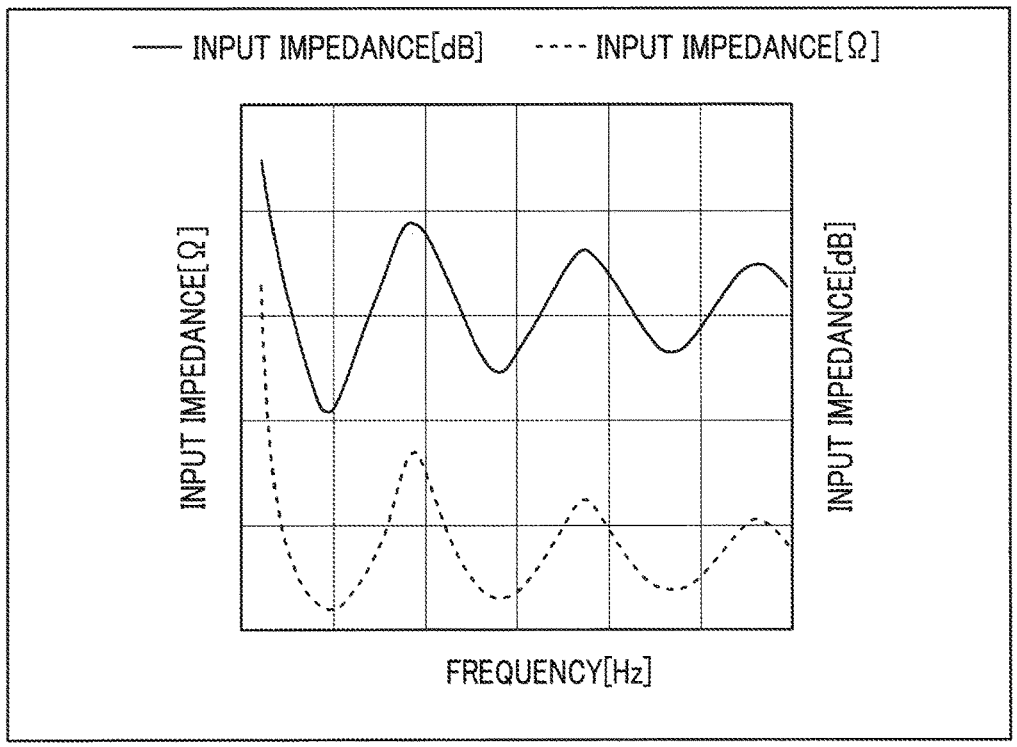
FIG. 4A is a diagram showing an example of an input impedance characteristic.
Figure 4B:
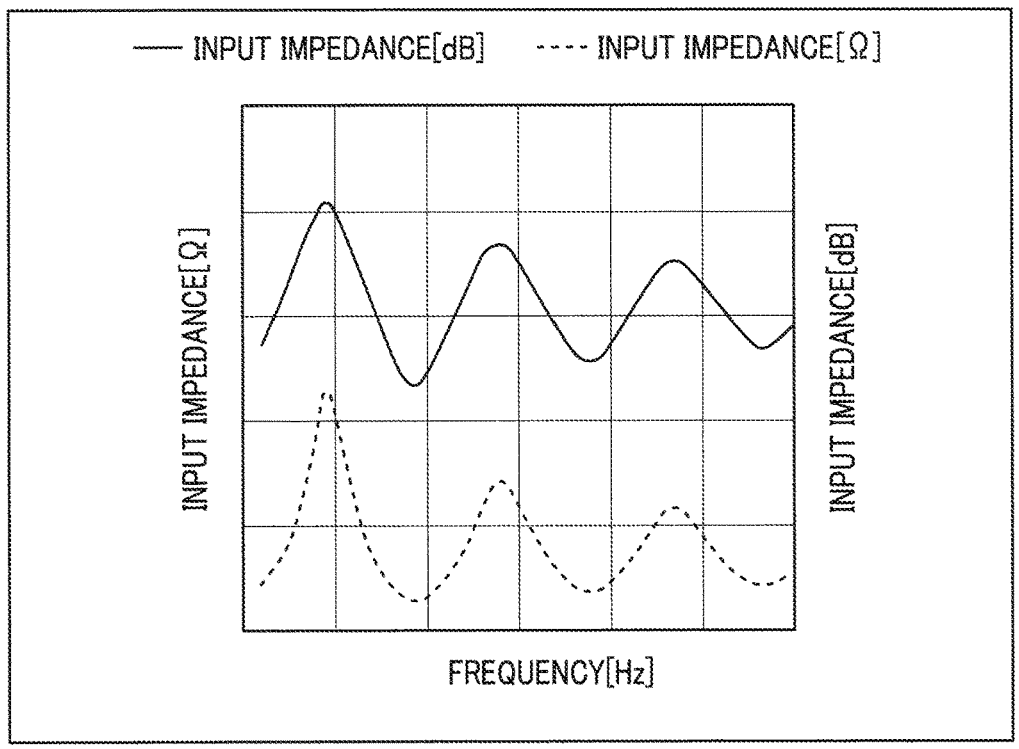
FIG. 4B is a diagram showing an example of the input impedance characteristic.
Figure 4C:
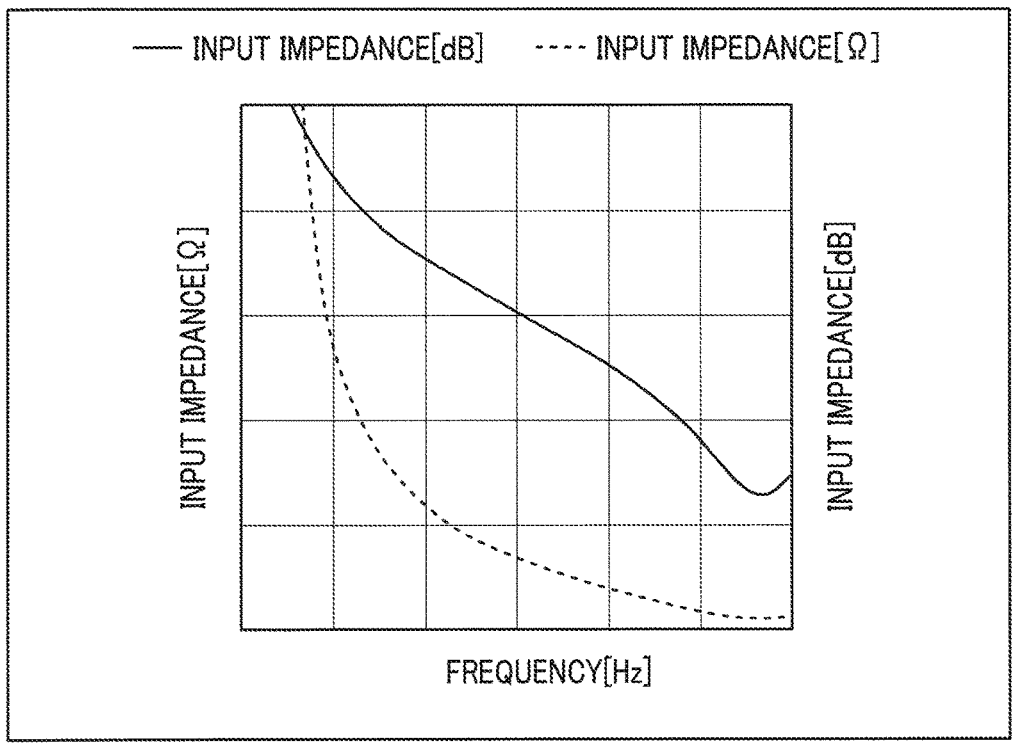
FIG. 4C is a diagram showing an example of the input impedance characteristic.
Figure 4D:
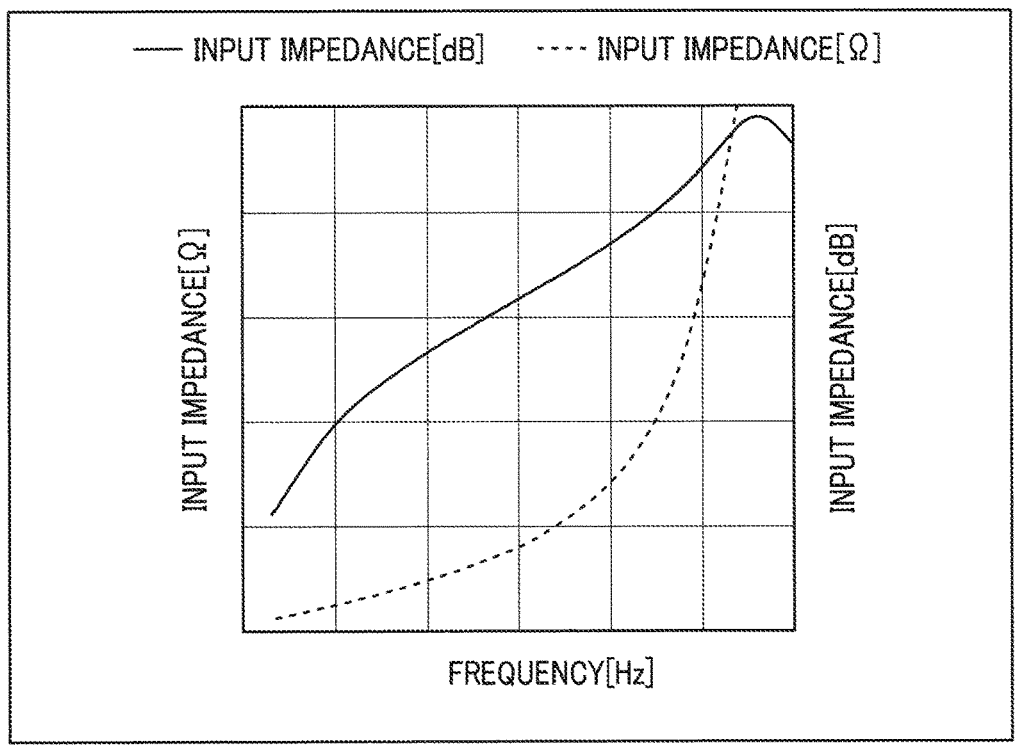
FIG. 4D is a diagram showing an example of the input impedance characteristic.

The input impedance characteristic of FIG. 4A shows the change of the input impedance with respect to the change of the frequency when the cable length s is long and the value of the identification resistor R1 is large. The input impedance characteristic of FIG. 4B shows the change of the input impedance with respect to the change of the frequency when the cable length s is long and the value of the identification resistor R1 is small. The input impedance characteristic of FIG. 4C shows the change of the input impedance with respect to the change of the frequency when the cable length s is short and the value of the identification resistor R1 is large. The input impedance characteristic of FIG. 4D shows the change of the input impedance with respect to the change of the frequency when the cable length s is short and the value of the identification resistor R1 is small.

When the load impedance of the optical adaptor 8 is equal to the characteristic impedance of the transmission cable 26, the value of the input impedance becomes a constant value regardless of the frequency. Frequency characteristics which are reversed to each other with the above state as a boundary are obtained in a case where the load impedance is larger than the characteristic impedance (FIGS. 4A and 4C) and a case where the load impedance is smaller than the characteristic impedance (FIGS. 4B and 4D), respectively. Even when the cable length s is changed, frequency characteristics in which the input impedance with respect to the frequency is reversed are also obtained. Since an effective cable length s increases or decreases depending on the magnitude of the dielectric constant of the transmission cable, for the rigorous processing the cable length s is converted into an effective cable length s and then used for calculation.

When the type of the optical adaptor 8 is determined by using the alternating current signal from the second optical adaptor type determination circuit 42, the CPU 20 uses the input impedance characteristics of FIGS. 4A to 4D. The CPU 20 changes the frequency of the alternating current signal to be applied to the identification unit 31 of the optical adaptor 8 according to the length s of the cable 26. Information on the cable length s of the transmission cable 26 incorporated in the endoscope apparatus 1 is stored in advance in the identification memory unit 21b. When the identification processing of the optical adaptor is performed, the information on the cable length s can be read by the CPU 20. The CPU 20 determines the frequency of the alternating current signal for controlling the second optical adaptor type determination circuit 42 so that the frequency of the alternating current signal is an optimal value corresponding to the cable length s read from the identification memory unit 21b. When the determination is performed, such a method is adopted as considering the input impedance characteristics as shown in FIGS. 4A to 4D, and pre-storing a correspondence table for the optimum frequency for each cable length in the memory unit 21a or the identification memory unit 21b, and referring to the table. Note that in addition to the cable length s, for example, the characteristic impedance Z0 and the propagation constant γ, or the electrical characteristic of the cable such as RLCG which is a source of the characteristic, or material information such as the thickness (diameter) and dielectric constant of the cable which are sources of the characteristic are stored as the cable characteristic information in the identification memory unit 21b, and can be read out appropriately by the CPU 20.

As shown in Equations (1) to (3), what value the input impedance will take can be estimated from the frequency of the alternating current signal, the load impedance, and the cable characteristic information. As a result, the CPU 20 measures the input impedance and carries out an operation by using the cable characteristic information read out from the identification memory unit 21b, whereby the load impedance, that is, the value of the identification resistor R1 of the optical adaptor 8, can be recognized, and the type of the optical adaptor 8 can be determined.

For example, a method can be considered in which Equation (1) for the impedance z1 of the load side (optical adaptor 8) is solved, the impedance z1 of the load side is calculated based on the measured input impedance Z(s) and the cable characteristic information (the cable length s, the characteristic impedance z0 and the propagation constant γ) read out from the identification memory unit 21b, and the CPU20 determines the type of the optical adaptor 8 according to the calculated impedance z1 of the load side (the resistance value of the identification resistor R1). As another method, an identification table in which the relationship between the input impedance Z(s) and the resistance value of the identification resistor R1 (the impedance z1 of the load side) is tabulated is stored in advance in the identification memory unit 21b, and the CPU 20 determines the resistance value of the identification resistor R1 by referring to the identification table stored in the identification memory unit 21b, thereby determining the type of the optical adaptor 8.

Figure 5B:
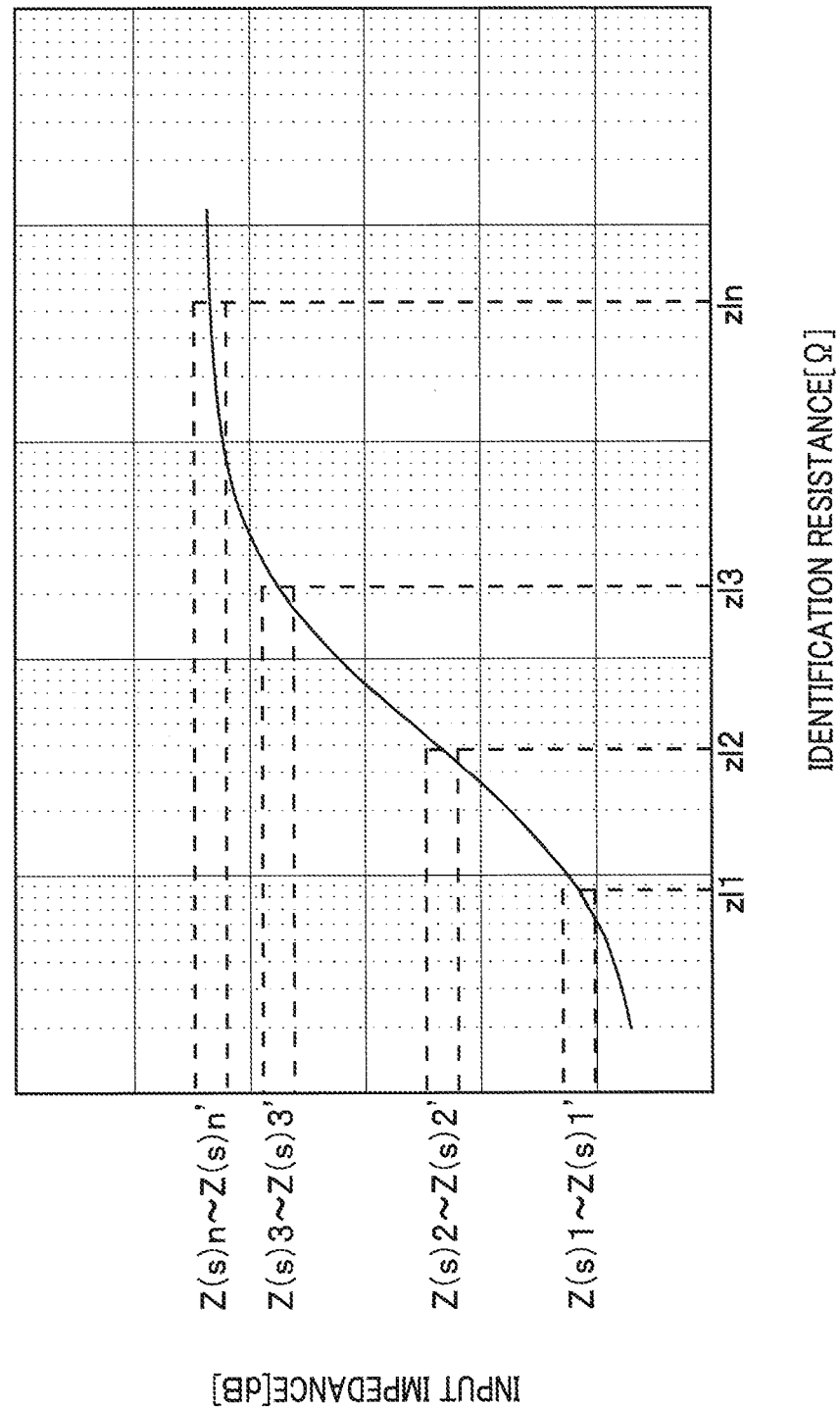
FIG. 5B is a diagram showing an example of the relationship between the input impedance and the resistance value of the identification resistor.

FIG. 5A is a diagram showing an example of the identification table in which the relationship between the input impedance and the resistance value of the identification resistor is tabulated, and FIG. 5B is a diagram showing an example of the relationship between the input impedance and the resistance value of the identification resistor.

As shown in FIGS. 5A and 5B, the CPU 20 determines that the resistance value of the identification resistor R1 is zl1 when the input impedance Z(s) is in the range of Z(s)1 to Z(s)1'. Furthermore, the CPU 20 determines that the resistance value of the identification resistor R1 is zl2 when the input impedance Z(s) is in the range of Z(s)2 to Z(s)2'.

Likewise, the CPU 20 determines that the resistance value of the identification resistor R1 is zl3 when the input impedance Z(s) is in the range of Z(s)3 to Z(s)3', and the CPU 20 determines that the resistance value of the identification resistor R1 is zln when the input impedance Z(s) is in the range of Z(s)n to Z(s)n'. Note that the input impedance Z(s) is defined, for example, in the range of Z(s)n to Z(s)n' because it is assumed that the input impedance Z(s) is varied due to the dispersion in length and structure of the transmission cable 26, temperature variation, etc.

Note that although the information necessary for the identification processing is described as being stored in the identification memory unit 21*b*, the present invention is not limited only to this style. In connection with the configuration of the endoscope apparatus 1, a part or all the information necessary for the identification processing may also be stored in the memory unit 21*a*.

Figure 6:
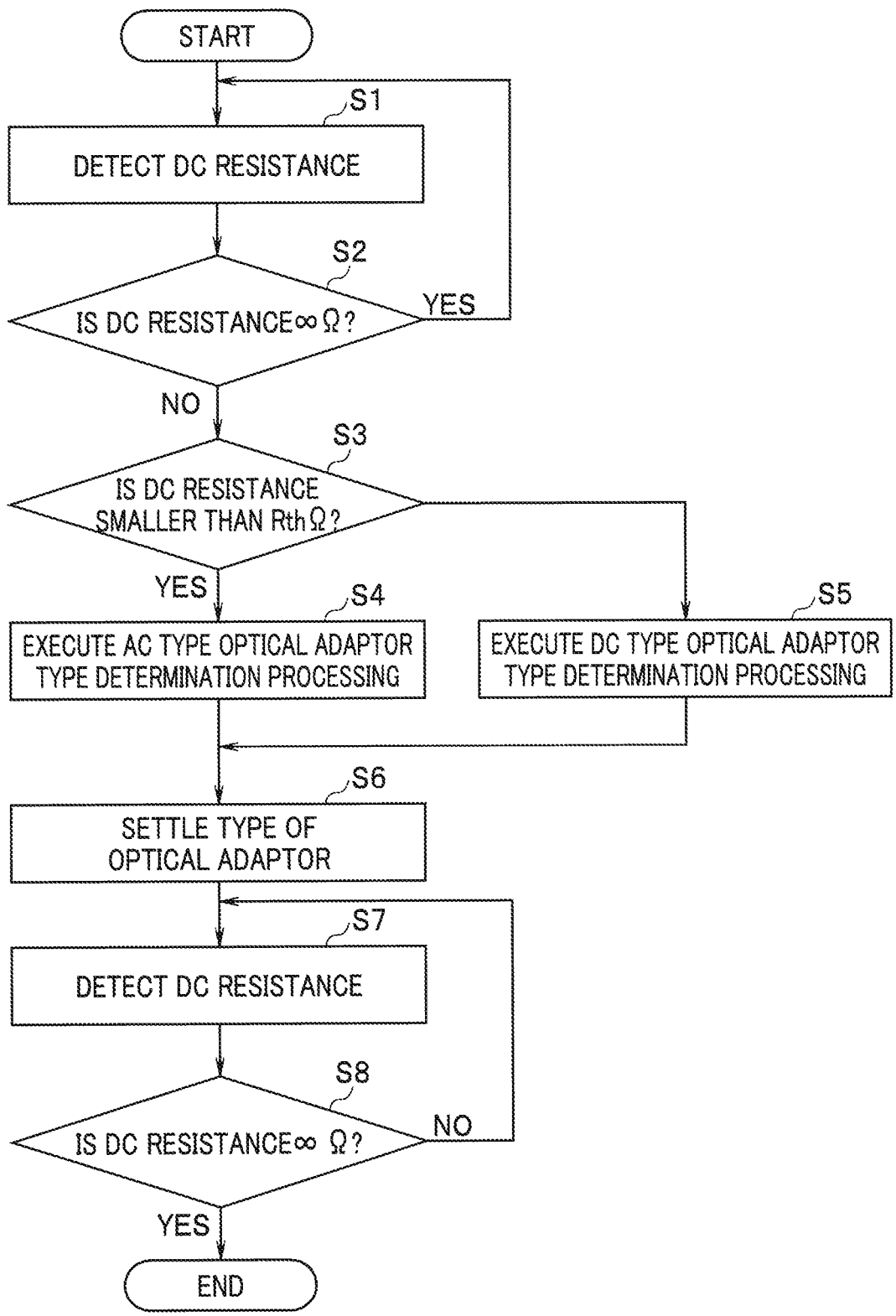
FIG. 6 is a flowchart showing an example of identification processing of the optical adaptor 8 of the endoscope apparatus 1 of the present embodiment.

Next, the identification processing of the optical adaptor 8 of the endoscope apparatus 1 of the present embodiment will be described. FIG. 6 is a flowchart showing an example of the identification processing of the optical adaptor 8 of the endoscope apparatus 1 of the present embodiment.

First, the CPU 20 transmits a selection signal to the switching circuit 43, and controls the switching circuit 43 so that the first optical adaptor type determination circuit 41 is connected to the transmission cable 26. As a result, a DC voltage is applied to the transmission cable 26 from the first optical adaptor type determination circuit 41, and the CPU 20 detects the direct current resistance (S1). The CPU 20 determines whether the detected direct current resistance is ∝Ω or not (S2). When the CPU 20 determines that the direct current is ∝Ω (S2: YES), the CPU 20 returns the processing to S1 to repeat the same processing. In other words, when the direct current resistance is ∝Ω, the CPU 20 determines an open state in which nothing is connected to the distal end portion 4, and thus determines that the optical adaptor 8 is not mounted.

On the other hand, when the CPU 20 determines that the direct current resistance is not ∝Ω (S2: NO), the CPU 20 determines whether the direct current resistance is smaller than Rth Ω (predetermined threshold value) (S3). In other words, when the direct current resistance is not ∝Ω, the CPU 20 determines a state where the optical adaptor 8 (or the optical adaptor 8*a*) is connected to the distal end portion 4, and thus performs the processing of determining the type of the optical adaptor 8 subsequent to S3. The CPU 20 determines in step S3 whether the direct current resistance is smaller than a predetermined threshold value, thereby determining whether the optical adapter is the optical adaptor 8 in which the MMA 33 is incorporated or the optical adaptor 8*a* in which no MMA is incorporated.

When the direct current resistance is smaller than Rth Ω (S3: YES), the CPU 20 determines that the optical adaptor is the optical adaptor 8 in which the MMA is incorporated, and executes the type identification processing of an alternating current method (S4). In other words, the CPU 20 transmits a selection signal to the switching circuit 43, and controls the switching circuit 43 so that the second optical adaptor type determination circuit 42 is connected to the transmission cable 26. As a result, the alternating current signal outputted from the sine-wave generation circuit 70 is applied to the optical adaptor 8. As described above, the CPU 20 determines the type of the optical adaptor 8 by measuring the input impedance.

On the other hand, when the direct current resistance is not less than Rth (S3: NO), the CPU 20 determines that the optical adaptor is the optical adaptor 8*a* in which no MMA is incorporated, and executes the type identification processing of a direct current method (S5). As described above, the CPU 20 determines in S3 whether the optical adaptor is the optical adaptor 8 in which the MMA is incorporated, and in the case of the optical adaptor 8 in which the MMA is incorporated, the CPU 20 executes the type identification processing of the alternating current method. In the case of the optical adaptor 8*a* in which no MMA is incorporated, the CPU 20 executes the type identification processing of the direct current method. As a result, the CPU 20 settles the type of the optical adaptor by the process of S4 or S5 (S6).

When the CPU 20 determines that the optical adaptor is the optical adaptor 8 in which the MMA is incorporated, the CPU 20 transmits the selection signal to the switching circuit 43 after determining the type of the optical adaptor 8, and controls the switching circuit 43 so that the MMA drive circuit 40 is connected to the transmission cable 26. As a result, the drive signal from the MMA drive circuit 40 is applied to the MMA 33 of the optical adaptor 8. Thereafter, the CPU 20 periodically transmits a selection signal to the switching circuit 43, and controls the switching circuit 43 so that the first optical adaptor type determination circuit 41 is periodically connected to the transmission cable 26. As a result, a DC voltage is periodically applied to the optical adaptor 8, and processing of detecting whether the optical adaptor 8 has been detached from the distal end portion 4 is executed.

The CPU 20 detects the direct current resistance (S7), and determines whether the direct current resistance is ∝Ω (S8). When determining that the direct current resistance is not ∝Ω (S8: NO), the CPU 20 determines that the optical adaptor 8 has not been detached from the distal end portion 4, and returns to S7 to repeat the same processing. On the other hand, when determining the direct current is ∝Ω (S8), CPU 20 determines that the optical adaptor 8 has been detached from the distal end portion 4, and ends the processing.

As described above, in the processing of S1 and S2, it is determined whether the optical adaptor 8 or 8*a* is mounted at the distal end portion 4. When the optical adaptor 8 or 8*a* is mounted at the distal end portion 4, the type of the optical adaptor 8 or 8*a* is determined in the processing of S3 to S6. When the type of the optical adaptor 8 or 8*a* is identified, it is determined in S7 and S8 whether the optical adaptor 8 or 8*a* has been detached from the distal end portion 4, and when the optical adaptor 8 or 8*a* has been detached from the distal end portion 4, the processing is ended.

As described above, the endoscope apparatus 1 uses an alternating current determination method of determining the type of the optical adaptor 8 by using the alternating current signal from the second optical adaptor type determination circuit 42. As a result, for the optical adaptor 8 of the type in which the MMA 33 is incorporated, it is also possible to identify the type of the optical adaptor 8 in addition to the driving operation of the MMA 33. The driving operation of the MMA 33 and the function of identifying the type of the optical adaptor 8 can be realized by the two signal lines 26*a* and 26*b* to the optical adaptor 8 and the two connection terminals 36*a* and 36*b*.

Therefore, according to the endoscope apparatus of the present embodiment, even if the optical adaptor having electric contacts of two terminals is attached, it is possible to perform the driving of the actuator and the identification of the type of the optical adaptor.

The endoscope apparatus 1 of the present embodiment can perform the identification of the type of the optical adaptor 8 and the driving of the MMA 33 by using the common transmission cable 26, that is, a pair of signal lines 26*a* and 26*b*. Therefore, the endoscope apparatus 1 of the present embodiment can perform the determination of the type of the optical adaptor 8 and the driving of the MMA 33 while maintaining the small diameter of the insertion portion 2.

The endoscope apparatus 1 of the present embodiment uses a direct current determination method of determining the type of the optical adaptor 8 by using the direct current signal from the first optical adaptor type determination circuit 41 in combination with the alternating current determination method. As a result, the endoscope apparatus 1 can also determine the type of the optical adaptor 8a of the type in which no MMA is incorporated, and it is possible to increase the number of optical adaptors the types of which can be determined. The endoscope apparatus 1 can determine whether the optical adaptor 8 or 8a is mounted at the distal end portion 4 by using the direct current determination method in combination with the alternating current determination method. Furthermore, the endoscope apparatus 1 can determine whether the optical adaptor is an optical adapter of the type in which the MMA 33 is incorporated or an optical adaptor 8a of a type in which no MMA is incorporated by using the direct current determination method in combination with the alternating current determination method.

The coil used for the actuator (MMA) is an element having a resistance (resistance value) of about several Ω. When the actuator (MMA) and the identification resistor (identification unit) are connected in parallel, the value of the combined resistance of the actuator and the identification resistor becomes extremely small due to the influence of the resistance of the actuator (MMA), which results in a difficulty in detecting the value of the identification resistor (identification unit) from the apparatus main body side. However, in the present embodiment, the type of the optical adaptor 8 can be determined by adopting the alternating current determination method of determining the type of the optical adaptor 8 by using the alternating current signal.

If the actuator (MMA) and the identification resistor (identification unit) are connected in series, the value of the drive current of the actuator becomes large value of several 100 mA, which results in a voltage drop and an energy consumption increase in the identification resistor. However, in the present embodiment, the actuator (MMA) and the identification resistor (identification unit) are connected in parallel, which prevents the voltage drop and the energy consumption increase in the identification resistor.

Thus, according to the present embodiment, even if it is supposed that an optical adaptor having electric contacts of two terminals is attached to the endoscope apparatus, it is possible to provide the endoscope apparatus including both functions of driving of the actuator and the identification of the type of the optical adaptor.

In addition, also in the method in which an output of an oscillation circuit is used as disclosed in the Japanese Patent Application Laid-Open Publication No. 2013-254034, if the actuator (MMA) is connected in parallel to the oscillation circuit, power source current flows in the actuator (MMA), which results in substantial difficulty in operating the oscillation circuit. However, in the present embodiment, when an alternating current is applied from the sine-wave generation circuit 70, the impedance of the capacitor C1 is set to a constant that is sufficiently negligible. That is, only the resistance value of the identification resistor R1 can be detected, and the type of the optical adaptor 8 can be determined according to the detected resistance value.

Therefore, according to the endoscope apparatus of the present embodiment, even if the optical adaptor having electric contacts of two terminals is attached, it is possible to perform both the driving of the actuator and the identification of the type of the optical adaptor.

Second Embodiment

Next, a second embodiment will be described. In the second embodiment, an endoscope apparatus 1 capable of enhancing the accuracy of determination of the type of the optical adaptor 8 in the alternating current determination method as compared with the first embodiment will be described. A configuration of the endoscope apparatus 1 of the second embodiment is similar to the configuration of the endoscope apparatus 1 of FIGS. 1 and 2.

The endoscope apparatus 1 according to the first embodiment measures the input impedance by using an alternating current signal having a certain frequency to determine the type of the optical adaptor 8. In this alternating current determination method, it is necessary to measure the impedance further in consideration of the cable characteristic of the transmission cable 26.

The change of the input impedance with respect to the frequency of the alternating current signal has been described with reference to the characteristic diagrams of FIGS. 4A to 4D, but this frequency-dependent characteristic fluctuates in a frequency axis direction due to the influence of the cable length s of the transmission cable 26 and the characteristic impedance (dielectric constant) of the transmission cable 26

For example, in the endoscope apparatus 1, it is assumed that the length of the transmission cable 26 varies or the length of the transmission cable 26 is changed due to dispersion in manufacturing, repair or the like. When the length of the transmission cable 26 varies or is changed, the value of the input impedance measured at a certain frequency will increase or decrease, so that the accuracy of determination of the type of the optical adaptor 8 may decrease.

Therefore, in the endoscope apparatus 1 of the present embodiment, the frequency at which the input impedance is measured is increased to two points, and the load impedance of the optical adaptor 8 is detected from a value of a slope between two input impedances measured at the frequencies of certain two points (the amount of the change between the two input impedances) to determine the type of the optical adaptor 8. In other words, the second optical adaptor type determination circuit 42 applies the alternating current signal having two frequencies to the optical adaptor 8, the two frequencies being different from each other. The CPU 20 measures each input impedance when the alternating current signal of the two frequencies is applied to the optical adaptor 8, and detects the value of the slope to determine the type of the optical adaptor 8. Note that the frequency for measuring the input impedance is not limited only to two points, but may be three or more points.

Figure 7A:
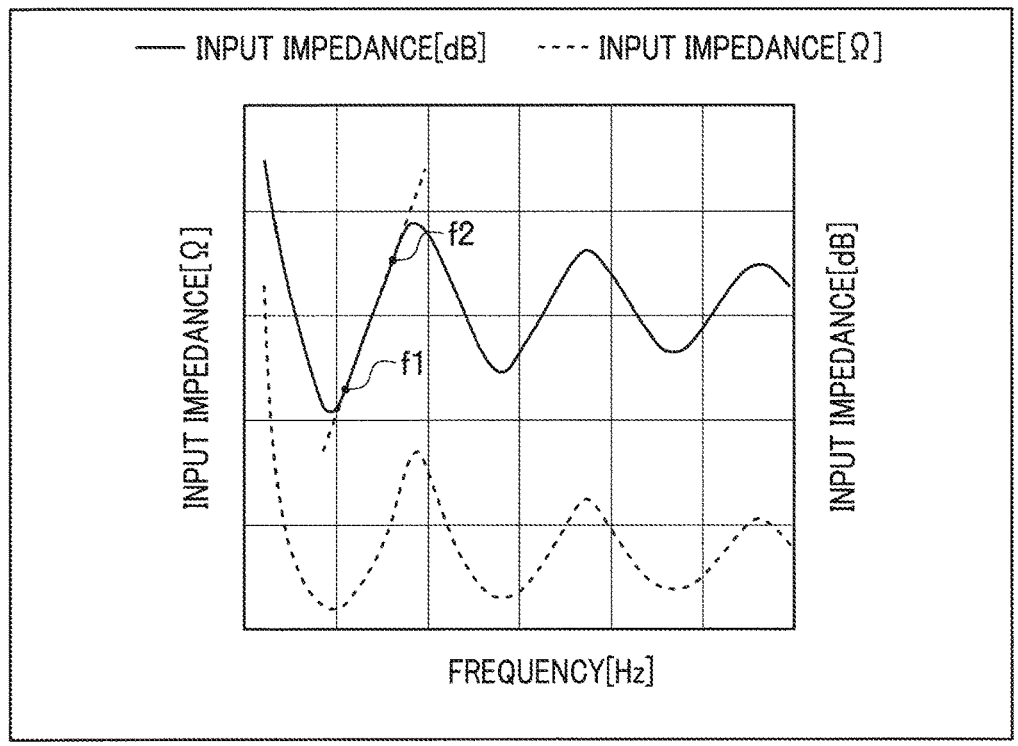
FIG. 7A is a diagram showing an example of the input impedance characteristic.
Figure 7B:
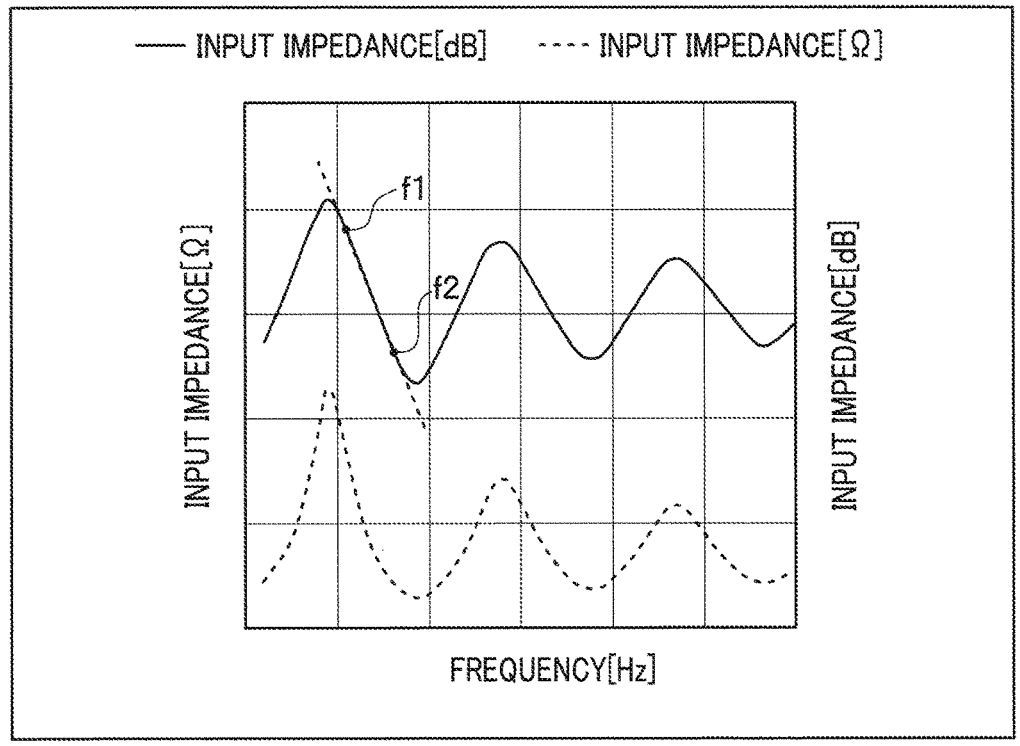
FIG. 7B is a diagram showing an example of the input impedance characteristic.

FIGS. 7A and 7B are diagrams showing examples of the input impedance characteristic. The input impedance characteristic of FIG. 7A shows the change of the input impedance with respect to the frequency change when the value of the identification resistor R1 of the optical adaptor 8 is large. The input impedance characteristic of FIG. 7B shows the change of the input impedance with respect to the frequency change when the value of the identification resistor R1 of the optical adaptor 8 is small.

When the value of the identification resistor R1 of the optical adaptor 8 is large, as shown in FIG. 7A, the value of the slope between the input impedance at a first frequency (identification frequency f1) of the alternating current signal and the input impedance at a second frequency (identification frequency f2) of the alternating current signal is positive.

On the other hand, when the value of the identification resistor R1 of the optical adaptor 8 is small, as shown in FIG. 7B, the value of the slope between the input impedance at the first frequency (identification frequency f1) of the alternating current signal and the input impedance at the second frequency (identification frequency f2) of the alternating current signal is negative.

As described above, the value of the slope between the input impedances changes according to the resistance value of the identification resistor R1 of the optical adaptor 8. The relationship between the resistance value of the identification resistor R1 and the value of the slope between the input impedances is shown in FIG. 8.

Figure 8:
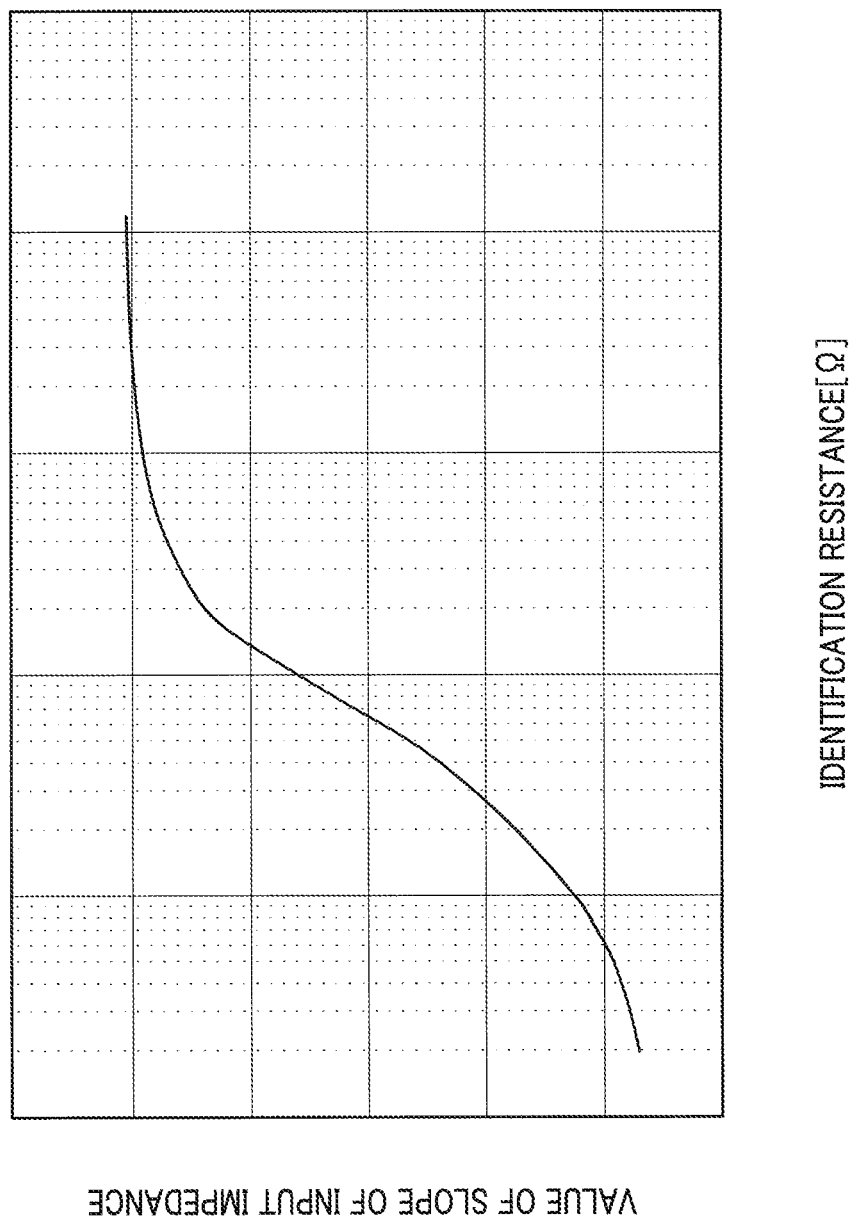
FIG. 8 is a diagram showing the relationship between the resistance value of an identification resistor R1 and a value of a slope between the input impedances.

FIG. 8 is a diagram showing the relationship between the resistance value of the identification resistor R1 and the value of the slope between the input impedances. A graph shown in FIG. 8 is obtained by continuously changing the resistance value of the identification resistor R1 of the optical adaptor 8 and plotting the value of the slope between the input impedances at that time.

An identification table (for example, an identification table as shown in FIG. 5A) in which the resistance value of the identification resistor R1 and the value of the slope between the input impedances shown in FIG. 8 are associated with each other is stored in the identification memory unit 21b. The CPU 20 uses Equation (4) to calculate the value of the slope between the input impedances measured at the identification frequencies f1 and f2.

[Equation 4]

$$\text{Value of slope between input impedances} = \frac{\text{input impedance }(f1) - \text{input impedance }(f2)}{\text{identification frequency }f1 - \text{identification frequency }f2} \quad (4)$$

The CPU 20 can obtain the resistance value of the identification resistor R1 of the optical adaptor 8 with respect to the calculated value of the slope between the input impedances by referring to the identification table stored in the identification memory unit 21b. The CPU 20 determines the type of the optical adaptor 8 according to the resistance value of the identification resistor R1.

As described above, the endoscope apparatus 1 according to the present embodiment determines the type of the optical adaptor 8 by using the value of the slope between the input impedances measured at the two identification frequencies f1 and f2. As a result, even when variation of the input impedance occurs in the frequency axis direction, the endoscope apparatus 1 of the present embodiment can accurately detect the resistance value of the identification resistor R1 without being affected by the variation.

As a result, the endoscope apparatus 1 of the present embodiment can more accurately determine the type of the optical adaptor 8 than the endoscope apparatus 1 of the first embodiment.

Note that the steps in the flowchart of the specification may be executed with the execution order being changed, a plurality of steps may be executed simultaneously, or the steps may be executed in a different order for each execution as long as these executions are not against the properties of the steps.

The present invention is not limited only to the above-described embodiments or modifications, but various changes, modifications, and the like can be made without departing from the subject matter of the present invention.

The present application claims priority based on Japanese Patent Application No. 2017-6459 filed on Jan. 18, 2017, and the above disclosure content is hereby incorporated by reference into the specification and the claims of the present application.

What is claimed is:

1. An endoscope apparatus comprising:
   an insertion portion configured to be alternately attached to at least one of:
      a first optical adaptor comprising a first identification circuit; and
      a second optical adaptor comprising a second identification circuit and an actuator electrically connected in parallel to the second identification circuit;
   a pair of conductive wires provided in the insertion portion;
   a direct current voltage source configured to apply a direct current voltage through the pair of conductive wires;
   an oscillation circuit configured to apply an alternating signal through the pair of conductive wires;
   a switching circuit configured to be controlled to connect one of the direct current voltage source and the oscillation circuit to the pair of conductive wires; and
   a processor configured to:
      control the switching circuit to connect direct current voltage source to the pair of conductive wires to apply the direct current voltage to one of:
         the first identification circuit in a state where the first optical adaptor is attached to the insertion portion; and
         the second identification circuit and the actuator in a state where the second optical adaptor is attached to the insertion portion;
      determine which of the first optical adaptor and the second optical adaptor is attached to the insertion portion based on a first measurement result obtained by applying the direct current voltage;
      in response to determining that the first optical adaptor is attached to the insertion portion, determine a type of the first optical adaptor based on the first measurement result; and
      in response to determining that the second optical adaptor is attached to the insertion portion,
         control the switching circuit to connect the oscillation circuit to the pair of conductive wires to apply the alternating signal to the second optical adaptor; and
         determine a type of the second optical adaptor based on a measurement result obtained by applying the alternating signal to the second optical adaptor.

2. The endoscope apparatus according to claim 1, wherein the processor is configured to determine the type of the second optical adaptor according to the measurement result obtained by applying the alternating signal to the second optical adaptor and a characteristic of the pair of conductive wires.

3. The endoscope apparatus according to claim 1, wherein the oscillation circuit is configured to change a frequency of the alternating signal applied to the second identification circuit through the pair of conductive wires according to a characteristic of the pair of conductive wires.

4. The endoscope apparatus according to claim 1, wherein the oscillation circuit is configured to apply an alternating current signal having two different frequencies to the second identification circuit through the pair of conductive wires, and wherein the processor is configured to:
measure input impedances of the pair of conductive wires at the two different frequencies of the alternating current signal as the measurement result obtained by applying the alternating signal to the second optical adaptor; and
determine the type of the second optical adaptor based on input impedances of the pair of conductive wires measured.

5. The endoscope apparatus according to claim 4, wherein the processor is configured to determine the type of the second optical adaptor based on an amount of change between the input impedances of the pair of conductive wires measured.

6. The endoscope apparatus according to claim 1, wherein the second identification circuit comprises a capacitor configured to prevent inflow of a drive signal into the second identification circuit when the drive signal is applied to the actuator.

7. The endoscope apparatus according to claim 1, further comprising: a resistor connected in series to the first identification circuit,
wherein the processor is configured to measure a voltage divided by the first identification circuit and the resistor as the first measurement result.

8. The endoscope apparatus according to claim 7, wherein the processor is configured to determine the type of the first optical adaptor based on a value of the voltage measured.

9. The endoscope apparatus according to claim 7, wherein the processor is configured to determine, based on a value of the voltage measured, which of the first optical adaptor and the second optical adaptor is attached to the insertion portion.

10. The endoscope apparatus according to claim 7, wherein the processor is configured to:
perform a comparison of a value of the voltage measured with a predetermined threshold value; and
determine which of the first optical adaptor and the second optical adaptor is attached to the insertion portion based on a result of the comparison.

11. The endoscope apparatus according to claim 2, wherein the characteristic of the pair of conductive wires includes at least one of a length of the pair of conductive wires, a diameter of the pair of conductive wires, a material of the pair of conductive wires, a characteristic impedance, and a propagation constant.

12. The endoscope apparatus according to claim 1, wherein the processor is configured to measure at least one of an input current and an input voltage of the pair of conductive wires.

13. The endoscope apparatus according to claim 1, wherein a resistance value of the first identification circuit is in a range from kiloohms to megaohms,
wherein a resistance value of the second identification circuit in a range from several tens of ohms to hundreds of ohms, and
wherein a resistance value of the actuator is under ten ohms.

14. A method for operating an endoscope apparatus, wherein the endoscope apparatus comprises:
an insertion portion configured to be alternately attached to at least one of:
a first optical adaptor comprising a first identification circuit; and
a second optical adaptor comprising a second identification circuit and an actuator electrically connected in parallel to the second identification circuit;
a pair of conductive wires provided in the insertion portion;
a direct current voltage source configured to apply a direct current voltage through the pair of conductive wires;
an oscillation circuit configured to apply an alternating signal through the pair of conductive wires; and
a switching circuit configured to be controlled to connect one of the direct current voltage source and the oscillation circuit to the pair of conductive wires, and
wherein the method comprises:
controlling the switching circuit to connect direct current voltage source to the pair of conductive wires to apply the direct current voltage to one of:
the first identification circuit in a state where the first optical adaptor is attached to the insertion portion; and
the second identification circuit and the actuator in a state where the second optical adaptor is attached to the insertion portion;
determining which of the first optical adaptor and the second optical adaptor is attached to the insertion portion based on a first measurement result obtained by applying the direct current voltage;
in response to determining that the first optical adaptor is attached to the insertion portion, determining a type of the first optical adaptor based on the first measurement result; and
in response to determining that the second optical adaptor is attached to the insertion portion,
controlling the switching circuit to connect the oscillation circuit to the pair of conductive wires to apply the alternating signal to the second optical adaptor; and
determining a type of the second optical adaptor based on a measurement result obtained by applying the alternating signal to the second optical adaptor.

15. A non-transitory computer-readable storage medium storing a program for operating an endoscope apparatus,
wherein the endoscope apparatus comprises:
an insertion portion configured to be alternately attached to at least one of:
a first optical adaptor comprising a first identification circuit; and
a second optical adaptor comprising a second identification circuit and an actuator electrically connected in parallel to the second identification circuit;
a pair of conductive wires provided in the insertion portion;
a direct current voltage source configured to apply a direct current voltage through the pair of conductive wires;
an oscillation circuit configured to apply an alternating signal through the pair of conductive wires; and
a switching circuit configured to be controlled to connect one of the direct current voltage source and the oscillation circuit to the pair of conductive wires, and wherein the program causes a computer to at least perform:
  controlling the switching circuit to connect direct current voltage source to the pair of conductive wires to apply the direct current voltage to one of:
    the first identification circuit in a state where the first optical adaptor is attached to the insertion portion; and
    the second identification circuit and the actuator in a state where the second optical adaptor is attached to the insertion portion;
  determining which of the first optical adaptor and the second optical adaptor is attached to the insertion portion based on a first measurement result obtained by applying the direct current voltage;
  in response to determining that the first optical adaptor is attached to the insertion portion, determining a type of the first optical adaptor based on the first measurement result; and
  in response to determining that the second optical adaptor is attached to the insertion portion,
    controlling the switching circuit to connect the oscillation circuit to the pair of conductive wires to apply the alternating signal to the second optical adaptor; and
    determining a type of the second optical adaptor based on a measurement result obtained by applying the alternating signal to the second optical adaptor.

* * * * *